(12) United States Patent
McNeilly

(10) Patent No.: US 6,214,586 B1
(45) Date of Patent: Apr. 10, 2001

(54) METHOD FOR PURIFYING PLASMID DNA AND PLASMID DNA SUBSTANTIALLY FREE OF GENOMIC DNA

(75) Inventor: David S. McNeilly, Saugus, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 08/986,885

(22) Filed: Dec. 8, 1997

(51) Int. Cl.$^7$ .................................................. C07H 21/04
(52) U.S. Cl. ..................... 435/91.1; 435/252.8; 435/259; 536/25.4; 536/25.41
(58) Field of Search ................................ 435/91.1, 252.8, 435/259; 536/25.4, 25.41

(56) References Cited

U.S. PATENT DOCUMENTS

| | | | |
|---|---|---|---|
| 5,082,781 | * | 1/1992 | Yamagata et al. .................. 435/201 |
| 5,496,934 | * | 3/1996 | Shoseyov et al. .................. 536/23.7 |
| 5,561,064 | * | 10/1996 | Marquet et al. .................. 435/320.1 |
| 5,625,053 | * | 4/1997 | Kresheck et al. ................. 536/25.41 |
| 5,707,812 | * | 1/1998 | Horn et al. ............................... 435/6 |

* cited by examiner

*Primary Examiner*—Leon B. Lankford, Jr.
(74) *Attorney, Agent, or Firm*—Dike, Bronstein, Roberts & Cushman, LLP; Steven R. Lazar

(57) ABSTRACT

A method is described for purifying plasmid DNA from a mixture containing plasmid DNA and genomic DNA. A solution containing both plasmid DNA and genomic DNA is treated with at least 80% by weight saturation ammonium sulfate, thereby precipitating the genomic DNA and providing purified plasmid DNA in solution. Genomic DNA levels in the purified plasmid DNA product are less than 1% by weight based on the plasmid DNA. The purified plasmid DNA is suitable for use in humans.

16 Claims, No Drawings

METHOD FOR PURIFYING PLASMID DNA AND PLASMID DNA SUBSTANTIALLY FREE OF GENOMIC DNA

FIELD OF THE INVENTION

This invention relates to methods for purification of plasmid DNA, particularly large quantities of plasmid DNA, and more particularly to methods for separating plasmid DNA from genomic DNA that are capable of providing kilogram quantities of plasmid DNA substantially free of genomic DNA.

BACKGROUND OF INVENTION

Many genetic diseases are difficult or impossible to treat with small molecule drugs or with enzyme replacement therapy as with Gaucher's disease. Recent advances in biology have raised the possibility that gene therapy, replacement of a defective gene with a normal gene, may be possible. Thus researchers have been studying several promising methods to deliver normal copies of genes to cells containing defective ones.

One promising method of gene delivery to humans is to use a plasmid DNA/lipid complex. The plasmid, a closed circular form of bacterial DNA, contains the genetic material needed to correct a genetic defect.

In some cases, large quantities of plasmid DNA ("pDNA") will be required to provide effective treatment to a population of patients afflicted with certain types of genetic diseases. Thus, recovery from the process must be high and the process must be scaleable to allow for efficient, cost effective production. Furthermore, the plasmid DNA will have to be very highly purified to allow for repeat dose administration of the complex to these patients. Because the plasmids used in clinical applications are produced typically by bacteria, e.g., *E. Coli*, the purification process must efficiently separate bacterial endotoxin, protein, and genomic (chromosomal) DNA from plasmid DNA, at very large scale. Because bacterial chromosomal DNA and plasmid DNA are so similar the process needs to be particularly effective at removing this contaminant.

Current methods described in the literature, such as cesium chloride centrifugation, chromatography on hydroxyapatite, or chromatographic methods based on reverse phase or anion exchange HPLC have limitations that would make purification of kilogram quantities difficult, if not impossible.

Purification of pDNA by centrifugation using cesium chloride involves use of toxic and carciongenic compounds, making this method unsuitable for purification of products for use in humans. Further, this technique could not be scaled to kilogram quantities per run.

Hydroxyapatite chromatography suffers from drawbacks as well. Lot variability of hydroxyapatite media would make consistent purification of plasmid DNA difficult. Further, because hydroxyapatite has a double positive charge and cannot be deprotonated, the resin cannot be cleaned, making it unusable as a technique for purifying clinical grade material.

HPLC (high pressure liquid chromatography) techniques also suffer from scaleability problems. HPLC columns capable of purifying kilogram quantities of pDNA are not currently manufactured.

Thus, new and better methods continue to be sought for purifying pDNA and which are scaleable to produce kilogram quantities of plasmid DNA of sufficient purity to be used as a therapeutic in humans.

SUMMARY OF THE INVENTION

The present invention provides a method for producing, in up to kilogram quantities, plasmid DNA, sufficiently pure for use as a human therapeutic. The method comprises separating plasmid DNA from genomic DNA by treating a solution containing both plasmid DNA from genomic DNA with at least 80% by weight saturation with ammonium sulfate, thereby precipitating the genomic DNA and leaving the plasmid DNA in solution.

In preferred embodiments of the invention, purified plasmid DNA is obtained that has less than 1% by weight genomic DNA by Southern Blot testing, more preferably no detectable genomic DNA, more preferably less than 0.2% by weight genomic DNA.

In one embodiment of the invention, a method for purifying plasmid DNA from a culture of cells comprises: lysing the cells; precipitating the bulk of contaminating cellular components to obtain a clarified lysate containing the plasmid DNA; concentrating the clarified lysate using a 100,000 molecular weight cutoff membrane; diafiltering the concentrated lysate into a suitable buffer; and precipitating from the diafiltered lysate both bacterial genomic DNA and RNA by the addition of ammonium sulfate, thereby providing a supernatant containing purified plasmid DNA. The lysing step can be performed on the cells directly from a fermenter or on the cells after the cells have been harvested by centrifugation then resuspended in a suitable buffer. Preferably, the step of lysing the cells and the step of precipitating the bulk of contaminating cellular components are both performed using static mixers.

In another embodiment of the invention, bacterial cells are lysed by simultaneously flowing a cell suspension and a lysis solution through a static mixer. Thousands of liters of a cell resuspension, containing hundreds of kilograms of cells can be lysed in a rapid and efficient manner using this technique. The bulk of contaminating cellular components including proteins, endotoxins and a substantial portion of the genomic DNA, are precipitated by simultaneously flowing the cell lysate and a precipitating solution through a static mixer. After removal of the precipitate by either filtration or centrifugation, the supernatant is ultrafiltered by tangential flow ultrafiltration using a 100,000 MW cutoff membrane. After the supernatant is concentrated, the material is diafiltered using a diafiltration buffer. When diafiltration is complete, ammonium sulfate is added to the retentate to a saturation of at least about 80%. After stirring, the precipitate, which contains RNA and bacterial genomic DNA, is removed by centrifugation. The resulting ammonium sulfate supernatant is loaded onto a column containing a reverse phase resin equilibrated with a buffer. After washing the column to reduce the amount of nicked plasmid, the plasmid DNA is eluted from the column. Finally, the pDNA containing reverse phase pool is loaded onto a column containing an anion exchange resin equilibrated with buffer. After washing the column to remove contaminants, the purified plasmid DNA is eluted from the column. At this stage, the plasmid DNA is highly purified and suitable for use in humans.

The methods of the present invention are capable of providing large (i.e., kilogram) quantities of clinical quality pDNA in a relatively efficient and cost-effective manner. Further, preferred embodiments of the present invention permits one to eliminate harvesting of the cells from the fermentor and to eliminate the separate precipitation of RNA with ammonium acetate.

DETAILED DESCRIPTION OF THE INVENTION AND PREFERRED EMBODIMENTS

The purification process of the present invention is capable of producing up to kilogram quantities of pDNA having sufficient purity for use as a human therapeutic. First, plasmid containing bacterial cells are lysed. Large volumes of cell suspensions can be lysed gently by use of static mixers as described in the U.S. patent application Ser. No. 08/632,203, filed on Apr. 15, 1996 now U.S. Pat. No. 5,837,529 and titled "Method of Lysing Cells," the disclosure of which is hereby incorporated by reference. After collection, the precipitated lysate is clarified, e.g., by centrifugation.

After clarification, it is generally desirable to lower the salt concentration to an appropriate level. This procedure is preferably performed using a tangential flow ultrafiltration device. It has been found that much of the contaminating material can be removed in the filtrate during desalting. Commercially available tangential flow ultrafiltration devices are suitable for this operation. A membrane having a 100,000 molecular weight cutoff is preferable, because it will be able to process a wide range of different sized plasmids, but devices with other porosites could be used depending on the size of the plasmid. After concentration to a suitable volume, preferably the material is diafiltered into a buffer appropriate for further processing. Preferably, the clarified lysate is concentrated about 10 fold, more preferably at least 15 fold. A suitable solution for diafiltration is made with 50 mM acetate, pH 5.4, and 1 mM EDTA (ethylenediaminetetraacetic acid).

The retentate at his point still contains the desired plasmid DNA, but is contaminated with genomic DNA and RNA. Solid ammonium sulfate is added to the ultrafiltration retentate to provide a concentration of about 80% by weight of the total amount of ammonium sulfate required to fully saturate the solution (i.e., 80% by weight saturation). Preferably, the ammonium sulfate is added in a stepwise fashion to maintain the pH of the precipitation step between about 5–7. After stirring slowly overnight at a temperature of about 4° C., the precipitate containing chDNA and RNA is removed by centrifugation and discarded.

Then, preferably the ammonium sulfate supernatant is loaded directly onto a column packed with a reverse phase resin. Reverse phase resins available from several manufacturers, including those from PerSeptive Biosystems, BioSepra, and YMC are suitable for this process. A preferred resin is Poros 50 R1, a column of which is equilibrated preferably with a solution of 50 mM acetate, pH 5.4, 1 mM EDTA, 80% saturation ammonium sulfate. The pDNA containing supernatant from the ammonium sulfate precipitation step is loaded onto the column. The column is washed preferably with a solution of 50 mM acetate, pH 5.4, 1 mm EDTA, 0.5 M NaCl, 2.85% ethanol. Plasmid DNA is eluted preferably with a solution of 50 mM acetate, pH 5.4, 1 mM EDTA, 0.5 M NaCl, 11.7% ethanol.

Another preferred reverse phase resin is an ion pairing resin sold under the trade name Puresyn PolyFlo.

The reverse phase pool is loaded directly onto a column packed with an anion exchange resin. Anion exchange resins available from several manufacturers, including those from PerSpective Biosystems, BioSepra, Pharmacia, BioRad, TosoHaas, and EM Sciences are suitable. A preferred resin is Poros 50 DE2, a column of which is equilibrated preferably with a solution of 50 mM acetate, pH 5.4, 1 mM EDTA, 0.5 M NaCl, 9.5% ethanol. The reverse phase pool containing pDNA is loaded onto the column. The column is washed preferably with a solution of 50 mM acetate, pH 5.4, 1 mM EDTA, 0.75 M NaCl, 9.5% ethanol. Plasmid DNA is eluted preferably with a solution of 50 mM acetate, pH 5.4, 1 mM EDTA, 1.4 M NaCl, 9.5% ethanol.

Preferred processes in accord with the present invention provide purified pDNA of very high purity. Bacterial endotoxin and protein levels are reduced to levels comparable to those found in other biopharmaceuticals used as human therapeutics. Bacterial genomic DNA (chDNA), a contaminant molecule that is very similar to pDNA is also effectively removed. Further, the precipitation step used to remove chDNA also unexpectedly removes RNA. Thus, no addition of bovine derived RNase is required. Another advantage of the process of the present invention is that large quantities of pDNA can be produced economically, using a minimum number of steps. Also, process recoveries are surprisingly high, further increasing throughout. All reagents and chromatographic resins that are used in preferred embodiments of the process are commercially available. Further, the chromatographic resins are not silica based and the only non-aqueous solvent used in preferred embodiments of the process is ethanol.

The contaminants of primary concern herein are endotoxins, proteins, genomic DNA and RNA. Endotoxin is measured by the LAL assay sold by Biowhittaker or by Associates of Cape Cod. Protein is measured using MICRO.BCA sold by Pearce Chemical of Rockford, Ill. RNA is visualized on 0.8% agarose gels (see Sambrook, Fritsch and Maniatis, *Molecular Cloning—A Laboratory Manual,* 2nd Edition, Cold Spring Harbor Laboratory Press (1989), particularly Chapter 6 "Gel Electrophoresis", Section 6.9 "Preparation and Examination of Agarose Gels"). Genomic (chromosomal) DNA is measured by the Southern Blot procedure.

Plasmid DNA product purified by preferred embodiments of the present invention contains less than 5 EU endotoxin, less than 1% by weight protein and less than 1% by weight genomic DNA, and RNA is undetectable on overloaded 0.8% agarose gels. More preferably, plasmid DNA in accord with the present invention contains less than 0.1% by weight protein and less than 0.2% by weight genomic DNA.

EXAMPLE 1

Prior Art

*Escherichia Coli* (*E. Coli*) cells that had been grown in a nutrient medium to a high cell density were centrifuged, then resuspended in a resuspending solution (50 mM Tris/HCl, pH 8.0, 10 mM EDTA) at a concentration of approximately 67 g cells /L. Alternatively, the nutrient broth containing unharvested *E Coli* cells was diluted 2:1 with resuspending solution (50 mM Tris/HCl, pH 8.0, 10 mM EDTA).

In either case, the cells were lysed using a static mixer as described in copending U.S. Ser. No. 08/632,203 (see above), and 2.6 M potassium acetate, pH 5.2 was added to precipitate much of the *E Coli* genomic DNA, protein, and other insoluble material is eliminated in the precipitate. The plasmid DNA remains in the soluble fraction.

The clarified lysate was concentrated 10–15 fold by tangential flow ultrafiltration using a device with a molecular weight cutoff of 100,000 daltons. The retained material (retentate) was then diafiltered with 7× approximate retentate volumes of diafiltration buffer (50 mM acetate, pH 5.4, 1 mM EDTA).

The solution was loaded onto an anion exchange column packed with Poros 50 DE2 resin (PerSeptive Biosystems, Framingham, Mass.) equilibrated with 50 mM acetate, pH 5.4, 1 mM EDTA, 0.5 M NaCl, 9.5% ethanol. After the column was washed with 20 column volumes of 50 mM acetate, pH 5.4, 1 mM EDTA, 0.75 M NaCl, 95% ethanol, the column was eluted with 50 mM acetate, pH 5.4, 1 mM EDTA, 1.4 M NaCl, 9.5% ethanol.

The eluate from the DE2 column was loaded directly onto a reverse phase column packed with Poros 50 R1 resin (PerSeptive Biosystems, Framingham, Mass.) equilibrated with a solution of 50 mM acetate, pH 5.4 1 mM EDTA, 80% by weight saturation ammonium sulfate. After the column was washed with 6 column volumes of 50 mM acetate, pH 5.4, 1 mM EDTA, 0.5 M NaCl, 2.85% ethanol, the column was eluted with 50 mM acetate, pH 5.4, 1 mM EDTA, 0.5 M NaCl, 11.7% ethanol, thereby obtaining the R1 Pool.

The R1 Pool was loaded onto a second anion exchange column packed with Poros 50 DE2 resin (PerSeptive Biosystems, Framingham, Mass.) equilibrated with 50 mM acetate, pH 5.4, 1 mM EDTA, 0.5 M NaCl, 9.5% ethanol. After the column was washed with 20 column volumes of 50 mM acetate, pH 5.4, 1 mM EDTA, 0.75 M NaCl, 95% ethanol, the column was eluted with 50 mM acetate, pH 5.4, 1 mM EDTA, 1.4 M NaCl, 9.5% ethanol. The eluate contains the purified *E. Coli* pDNA, which is ready for formulation.

In several runs producing different plasmids, the weight % genomic DNA (based on the plasmid DNA product) after the reverse phase R1 column step was 1.33, 9.79, 1.84, 0.93, 0.55, 2.17, 0.99, 1.24, 0.82, 0.83, 3.42, 3.02, 2.51, 0.54, 1.37, <0.2, and 0.72, respectively. It can be seen that the prior art process provides inconsistent removal of genomic DNA and the second DE2 column is normally required to reduce the amount of genomic DNA to acceptable levels.

EXAMPLE 2

*Escherichia Coli* (*E. Coli*) cells that had been grown in a nutrient medium to a high cell density were centrifuged, then resuspended in a resuspending solution (50 mM Tris/HCl, pH 8.0, 10 mM EDTA) at a concentration of approximately 67 g cells/L. Alternatively, the nutrient broth containing unharvested *E Coli* cells was diluted 2:1 with resuspending solution (50 mM Tris/HCl, pH 8.0, 10 mM EDTA).

In both cases, the cell suspension was pumped through a ½"×27", 32-element Kenics static mixer (purchased from Chemineer, N. Andover, Mass.) along with a lysis solution (200 mM NaOH, 1% SDS ("sodium dodecyl sulfate")). The pumps employed for this procedure were peristaltic pumps (Cole Parmer, Chicago Ill.). The flow rate of both solutions to the mixer inlets was 500 mL/min. The lysate was collected in a suitable container and was allowed to stand for at least 10 minutes prior to further processing.

The lysate and precipitating solution were mixed together in a similar fashion. Lysate was pumped into one of two inlets of the static mixer (same as above) at a flow rate of 1000 mL/min. The precipitating solution (2.6 M potassium acetate, pH 5.2) was pumped simultaneously into the second inlet of the static mixer at a flow rate of 500 mL/min. The lysate containing precipitate was collected in a suitable container. The precipitate was removed either by filtration using suitable methods or by centrifugation. A clarified lysate suitable for further processing was obtained by either method.

At this stage much of the *E Coli* genomic DNA, protein, and other insoluble material is eliminated in the precipitate. The plasmid DNA remains in the soluble fraction.

The clarified lysate was concentrated 10–15 fold by tangential flow ultrafiltration using a device with a molecular weight cutoff of 100,000 daltons. The retained material (retentate) was then diafiltered with 7× approximate retentate volumes of diafiltration buffer (50 mM acetate, pH 5.4, 1 mM EDTA).

*E. Coli* genomic DNA and RNA were precipitated by addition of solid ammonium sulfate (ACS grade) at 80% by weight saturation. The pH of the solution was maintained at 5.2+/−0.2. The suspension was allowed to stir slowly overnight at 4° C. The resulting precipitate (containing the genomic DNA and RNA) was; removed by centrifugation at 10,000× g for 30 min.

The ammonium sulfate supernatant was loaded directly onto a reverse phase column packed with Poros 50 R1 resin (PerSeptive Biosystems, Framingham, Mass.) equilibrated with a solution of 50 mM acetate, pH 5.4 1 mM EDTA, 80% by weight saturation ammonium sulfate. After the column was washed with 6 column volumes of 50 mM acetate, pH 5.4, 1 mM EDTA, 0.5 M NaCl, 2.85% ethanol, the column was eluted with 50 mM acetate, pH 5.4, 1 mM EDTA, 0.5 M NaCl, 11.7% ethanol, thereby obtaining the R1 Pool.

The R1 Pool was loaded onto an anion exchange column packed with Poros 50 DE2 resin (PerSeptive Biosystems, Framingham, Mass.) equilibrated with 50 mM acetate, pH 5.4, 1 mM EDTA, 0.5 M NaCl, 9.5% ethanol. After the column was washed with 20 column volumes of 50 mM acetate, pH 5.4, 1 mM EDTA, 0.75 M NaCl, 95% ethanol, the column was eluted with 50 mM acetate, pH 5.4, 1 mM EDTA, 1.4 M NaCl, 9.5% ethanol. The eluate contains the purified *E. Coli* pDNA, which is ready for formulation.

In several runs producing different plasmids, the weight % genomic DNA (based on the plasmid DNA product) after the ammonium sulfate precipitation step was <1, <0.5, <0.5, <0.5, <0.5, <0.5, <1, <0.5, and <0.5, respectively. Typically, the weight % genomic DNA after the reverse phase step (following the ammonium sulfate precipitation) is <0.2, the limit of the measuring technique.

It can be seen that the process according to the present invention provides surprisingly and unexpectedly low genomic DNA in the plasmid product The invention has been described in detail with reference to preferred embodiments thereof. However, it will be appreciated that, upon consideration of the present specification and drawings, those skilled in the art may make modifications and improvements within the spirit and scope of this invention as defined by the claims.

I claim:

1. A method for purifying plasmid DNA from a mixture containing plasmid DNA and genomic DNA, said method comprising treating a solution containing both plasmid DNA and genomic DNA with at least 80% by weight saturation with ammonium sulfate, thereby precipitating the genomic DNA and providing s aid purified plasmid DNA in solution.

2. The method according to claim 1, wherein genomic DNA levels are less than 1% by weight based on the plasmid DNA in said purified plasmid DNA in solution.

3. The method according to claim 1, wherein genomic DNA levels are less than 0.2% by weight based on the plasmid DNA in said purified plasmid DNA in solution.

4. A method for purifying plasmid DNA from a culture of cells, said method comprising:

lysing the cells;

precipitating the bulk of contaminating cellular components to obtain a clarified lysate containing the plasmid DNA;

concentrating the clarified lysate using a 100,000 molecular weight cutoff membrane;

diafiltering the concentrated lysate into a suitable buffer; and precipitating from the diafiltered lysate both bacterial genomic DNA and RNA by the addition of ammonium sulfate:

thereby providing a supernatant containing purified plasmid DNA.

5. The method according to claim 4, wherein the lysing step is performed on the cells directly from a fermenter.

6. The method according to claim 4, wherein the lysing step is performed on the cells after the cells have been harvested by centrifugation then resuspended in a suitable buffer.

7. The method according to claim 4, wherein the step of lysing the cells and the step of precipitating the bulk of contaminating cellular components are both performed using static mixers.

8. The method according to claim 4, wherein the concentrating step is performed by tangential flow ultrafiltration using a 100,000 molecular weight cutoff membrane.

9. The method according to claim 4, further comprising treating the supernatant by reverse phase chromatography to obtain an eluant containing purified plasmid DNA.

10. The method according to claim 9, further comprising treating the eluant using anion exchange chromatography.

11. A method of purifying *E. coli* pDNA from a culture of cells, wherein said method is scaleable to kilogram quantities, said method comprising:

lysing the cells;

precipitating the bulk of contaminating cellular components to obtain a clarified lysate containing the plasmid DNA;

concentrating the clarified lysate using a 100,000 molecular weight cutoff membrane;

diafiltering the concentrated lysate into a suitable buffer; and precipitating from the diafiltered lysate both bacterial genomic DNA and RNA by the addition of ammonium sulfate;

thereby providing a supernatant containing purified plasmid DNA.

12. The method according to claim 11, wherein the lysing step is performed on the cells directly from a fermenter.

13. The method according to claim 11, wherein the lysing step is performed on the cells after the cells have been harvested by centrifugation then resuspended in a suitable buffer.

14. The method according to claim 11, wherein the concentrating step is performed by tangential flow ultrafiltration using a 100,000 molecular weight cutoff membrane.

15. The method according to claim 11, further comprising treating the supernatant by reverse phase chromatography to obtain an eluant containing purified plasmid DNA.

16. The method according to claim 15, further comprising treating the eluant using anion exchange chromatography.

* * * * *